United States Patent
Liou et al.

(10) Patent No.: US 12,129,279 B2
(45) Date of Patent: Oct. 29, 2024

(54) ANTIMICROBIAL PEPTIDES AND USE OF THE SAME FOR TREATING MICROBIAL INFECTIONS

(71) Applicant: TZU CHI UNIVERSITY, Hualien (TW)

(72) Inventors: Je-Wen Liou, Hualien (TW); Yu-Ren Chen, Hualien (TW); Chin-Hao Yang, Hualien (TW)

(73) Assignee: TZU CHI UNIVERSITY, Hualien (TW)

(*) Notice: Subject to any disclaimer, the term of this patent is extended or adjusted under 35 U.S.C. 154(b) by 0 days.

(21) Appl. No.: 18/061,355

(22) Filed: Dec. 2, 2022

(65) Prior Publication Data

US 2024/0182527 A1    Jun. 6, 2024

(51) Int. Cl.
| | |
|---|---|
| *A23L 33/18* | (2016.01) |
| *A61P 31/04* | (2006.01) |
| *C07K 14/00* | (2006.01) |

(52) U.S. Cl.
CPC ............ *C07K 14/001* (2013.01); *A23L 33/18* (2016.08); *A61P 31/04* (2018.01)

(58) Field of Classification Search
CPC ......... C07K 14/001; A23L 33/18; A61P 31/04
See application file for complete search history.

(56) References Cited

U.S. PATENT DOCUMENTS

2020/0270307 A1*  8/2020  Del'Guidice .......... C12N 15/90

OTHER PUBLICATIONS

Accession No. A0A6I6RIV6, accessed Mar. 13, 2024 at URL uniprot.org/uniprotkb/A0A6I6RIV6/entry. (Year: 2024).*
IQWiG, "What are microbes?," IQWiG (Institute for Quality and Efficiency in Health Care), 1 page, Accessed Mar. 14, 2024 at URL ncbi.nlm.nih.gov/books/NBK279387/?report=printable (2010) (Year: 2010).*
Doron ("Bacterial infections: Overview"; International Encyclopedia of Public Heatlh, 2008:273-282) (Year: 2008).*
CDC (https://www.cdc.gov/fungal/diseases/index.html accessed May 21, 2021) (Year: 2021).*
Merck Manual (https://www.merckmanuals.com/home/skin-disorders/fungal-skin-infections/overview-of-fungal-skin-infections accessed Feb. 19, 2019) (Year: 2019).*
Merck Manual—fungal infections overview (https://www.merckmanuals.com/professional/infectious-diseases/fungi/overview-of-fungal-infections accessed Oct. 21, 2020) (Year: 2020).*
Merck Manual (https://www.merckmanuals.com/professional/infectious-diseases/approach-to-parasitic-infections/approach-to-parasitic-infections?query=protozoa accessed Oct. 22, 2020 (Year: 2020).*
Merck Manual (https://www.merckmanuals.com/professional/infectious-diseases/viruses/overview-of-viruses accessed Feb. 19, 2019) (Year: 2019).*
Yang et al., "An engineered arginine-rich α-helical antimicrobial peptide exhibits broad-spectrum bactericidal activity against pathogenic bacteria and reduces bacterial infections in mice," scientific reports 8:14602, pp. 1-14 (2018).*

* cited by examiner

*Primary Examiner* — Julie Ha
*Assistant Examiner* — Kristina M Hellman
(74) *Attorney, Agent, or Firm* — Sughrue Mion, PLLC

(57) ABSTRACT

The present invention relates to novel antimicrobial peptides and compositions comprising the same. The present invention also provides a method for for treating microbial infections, including bacterial infections and fungal infections.

9 Claims, 13 Drawing Sheets

Specification includes a Sequence Listing.

SEQUENCE LISTING

```
Sequence total quantity: 5
SEQ ID NO: 1              moltype = AA  length = 22
FEATURE                   Location/Qualifiers
source                    1..22
                          mol_type = protein
                          organism = Synthetic construct
SEQUENCE: 1
IVRRIWRAWA RRVRLVARIP AV                                          22

SEQ ID NO: 2              moltype = AA  length = 22
FEATURE                   Location/Qualifiers
source                    1..22
                          mol_type = protein
                          organism = Synthetic construct
SEQUENCE: 2
RLIAAWRAVI RARVRARRAP IF                                          22

SEQ ID NO: 3              moltype = AA  length = 22
FEATURE                   Location/Qualifiers
source                    1..22
                          mol_type = protein
                          organism = Synthetic construct
SEQUENCE: 3
RPFIVRAWRR AVARRARAIL PI                                          22

SEQ ID NO: 4              moltype = AA  length = 22
FEATURE                   Location/Qualifiers
source                    1..22
                          mol_type = protein
                          organism = Synthetic construct
SEQUENCE: 4
FLPASFPAKF GPKLFCLVTK KC                                          22

SEQ ID NO: 5              moltype = AA  length = 22
FEATURE                   Location/Qualifiers
source                    1..22
                          mol_type = protein
                          organism = Synthetic construct
SEQUENCE: 5
FLAIPSKPLK VAKPLGFALI IL                                          22
```

ANTIMICROBIAL PEPTIDES AND USE OF THE SAME FOR TREATING MICROBIAL INFECTIONS

FIELD OF THE INVENTION

The present disclosure relates to novel antimicrobial peptides and their use in treating microbial infections.

BACKGROUND OF THE INVENTION

Abuse of antibiotics is a common problem in clinical practice, increasing medical costs and resulting in patient mortality. Given the prevalence and impact of drug-resistant bacteria, antibacterial peptides are emerging as promising candidates addressing such issues. The bactericidal mechanism primarily targets the amphipathic structures of the antibacterial peptides that allow them to interact directly with microbial membranes, which they can rapidly permeabilize. Specifically, the electrostatic interaction between the positively charged amino acids in the peptides and the negatively charged teichoic acid or peptidoglycan in the membrane of the bacteria prompts the hydrophobic interaction that contributes to the conformational change in the peptides. In this regard, antibacterial peptides apply bactericidal mechanisms different from traditional antibiotics, potentially eradicating drug-resistant bacteria.

Although a variety of antimicrobial peptides have been recently developed, only a few peptides could be designed effectively based on the physical properties obtained from the algorithm methods while maintaining safety and efficacy. Therefore, an efficient way of investigating antimicrobial peptides with high efficacy of antimicrobial activities against a wide spectrum of microorganisms is still needed.

SUMMARY OF THE INVENTION

The present invention provides peptides and/or compositions that exhibit a wide spectrum of antimicrobial activities. The present invention also provides methods for treating microbial infections.

In one aspect, the present invention provides a novel antimicrobial peptide comprising an amino acid sequence selected from the group consisting of SEQ ID NO: 1, SEQ ID NO: 2, and SEQ ID NO: 3.

In some embodiments, the antimicrobial peptide comprises the amino acid sequence set forth in SEQ ID NO: 1.

In some embodiments, the antimicrobial peptide comprises the amino acid sequence set forth in SEQ ID NO: 2.

In some embodiments, the antimicrobial peptide comprises the amino acid sequence set forth in SEQ ID NO: 3.

The present invention also provides nucleic acid molecules encoding the antimicrobial peptides and vectors and host cells for expressing the antimicrobial peptides of the present invention.

In one embodiment, the antimicrobial peptides are prepared by peptide synthesis. In another embodiment, the antimicrobial peptides are obtained from culturing the host cells of the present invention.

In some embodiments, the antimicrobial peptide of the invention is effective against a microorganism selected from Gram-positive bacteria, Gram-negative, bacteria and fungi.

In one embodiment, the Gram-positive bacterium is methicillin-resistant *Staphylococcus aureus* (MRSA).

In one embodiment, the Gram-negative bacterium is Multi-drug resistant *Acinetobacter* baumaanii (MDRAB).

In some embodiments, the antimicrobial peptides have an antimicrobial activity of $IC_{50} < 0.2$ μM, $IC_{50} < 0.25$ μM, $IC_{50} < 0.39$ μM or $IC_{50} < 3.12$ μM.

In some embodiments, the antimicrobial peptides have an antimicrobial activity of MBC<0.6 μM, MBC<0.78 μM, MBC<1.33 μM, or MBC<1.56 μ.

In another aspect, the present invention provides a composition comprising a novel antimicrobial peptide comprising an amino acid sequence selected from the group consisting of SEQ ID NO: 1, SEQ ID NO: 2, and SEQ ID NO: 3 or a mixture of the aforementioned antimicrobial peptides.

In still another aspect, the antimicrobial peptide of the invention is prepared as an antimicrobial agent.

In some embodiments, the antimicrobial agent is an oral formulation. In some embodiments, the antimicrobial agent is prepared as a formulation for injection.

In some embodiments, the antimicrobial agent is coated on a substrate to prevent microorganisms from attaching to or growing on the substrate.

In some embodiments, the antimicrobial agent is added to a food or feed to prevent the growth of harmful microorganism in the food or feed.

In another aspect, the present invention provides methods for treating microbial infections, comprising administering to a subject in need thereof a therapeutically effective amount of the antimicrobial peptides or compositions of the present invention.

The present invention is described in detail in the following sections. Other characterizations, purposes and advantages of the present invention can be easily found in the detailed descriptions and claims of the invention.

DETAILED DESCRIPTION OF THE INVENTION

Figure 1:
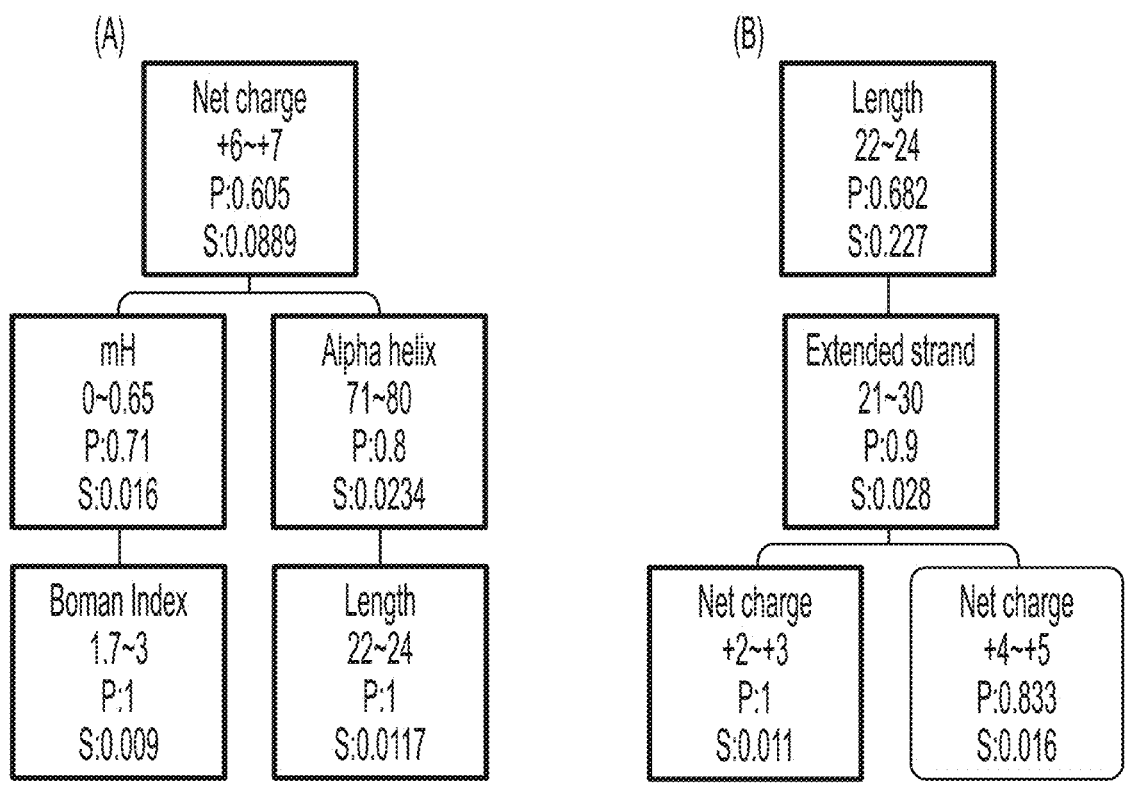
FIG. 1 shows the rules of the decision trees for peptides against Gram-positive bacteria and Gram-negative bacteria respectively. (A) The rules of the decision trees for α-helix peptides. (B) The rules of the decision trees for β-stranded peptides. "Net charge" in the decision tree represents the total charge of the peptide in an electrically neutral environment; "mH" is the hydrophobic moment of the peptide, which is used to represent the distribution of hydrophobic amino acid residues in the peptide; "Boman index" is the estimated value of the binding potential of the peptide to other proteins; "Length" is the length of the peptide; and "Alpha helix" and "Extended strand" represent the proportion of this structure in the peptide. The "P value" of each branch node represents the proportion of effective antimicrobial peptides that meet this characteristic, and the "S value" represents the proportion of antimicrobial peptides that meet the characteristics indicated in the branch node among the entire data set. The red frame marks the rules that should be followed in the decision tree.

The disclosed compositions and methods may be understood more readily by reference to the following detailed description of particular embodiments.

It is to be understood that the disclosed compositions and methods are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

INTRODUCTION

Accumulated information from numerous studies on the characteristics of antimicrobial peptides (AMPs) has provided clues for further AMP development. Although AMPs can adopt different conformational structures, including β-sheet and random-coil structures, most of them have α-helical structures [see Wang, G., Li, X. & Wang, Z. "APD3: the antimicrobial peptide database as a tool for research and education." *Nucleic Acids Research* 44, D1087-D1093, 2016; and Huang, Y., Huang, J. & Chen, Y. "Alpha-helical cationic antimicrobial peptides: relationships of structure and function." *Protein & cell* 1, 143-152, 2010]. AMPs also exhibit a certain degree of generalized properties, including amphipathicity, mean hydrophobicity, and net cationic charge [see Jenssen, H., Hamill, P. & Hancock, R. E. W. "Peptide Antimicrobial Agents." *Clinical Microbiology Reviews* 19, 491-511, 2006]. Although peptide amphipathicity is an important factor responsible for the interaction of peptides with amphipathic biological membranes, the net cationic nature of AMPs is suggested to be responsible for peptide selectivity [see Hollmann, A. et al. "Role of amphipathicity and hydrophobicity in the balance between hemolysis and peptide-membrane interactions of three related antimicrobial peptides." *Colloids and Surfaces B: Biointerfaces* 141, 528-536, 2016]. Positively charged AMPs interact strongly with negatively charged bacterial membranes that contain a large proportion of negatively charged molecules, including negatively charged lipids such as phosphatidylglycerol and cardiolipin, lipoteichoic acids in the peptidoglycan for Gram-positive bacteria, and lipopolysaccharides (LPSs) in the outer membrane for Gram-negative bacteria [see Li, P. et al. "Molecular mechanisms that govern the specificity of Sushi peptides for Gram-negative bacterial membrane lipids." *Biochemistry* 45, 10554-10562, 2006]. Because the outer leaflet of mammalian membranes contains mostly neutrally charged lipids, including sphingomyelin, phosphatidylcholine, and sterols [see Huang, J. & Chen, Y., 2010], the architectural differences between mammalian and bacterial membranes should provide a feasible means for cationic AMPs to selectively target bacteria.

Since most novel peptide drug developments fail between their identification and introduction to the market [see Uhlig, T. et al. "The emergence of peptides in the pharmaceutical business: From exploration to exploitation." *EuPA Open Proteomics* 4, 58-69, 2014], methodologies to effectively generate lead drugs for further tests should be developed.

Having now generally described the invention, the same may be more readily understood through reference to the following examples, which provide exemplary protocols for testing the effect of antimicrobial peptides designed with algorithm aided methods in the treatment of bacterial infections. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Definitions

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedence over any dictionary or extrinsic definition.

As utilized in accordance with the present disclosure, the following terms, unless otherwise indicated, shall be understood to have the following meanings.

The term "about" when used before a numerical designation, e.g., temperature, time, amount, concentration, and such other, including a range, indicates approximations which may vary by (+) or (−) 10%, 5% or 1%.

The term "comprising" or "comprises" is intended to mean that the compositions and methods include the recited elements, but not excluding others. "Consisting essentially of" when used to define medicaments and methods, shall mean excluding other elements of any essential significance to the combination for the stated purpose. Thus, a medicament or method consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "treating" or "treatment" as used herein denotes alleviating, relieving, reversing and/or improving a disorder or condition or one or more symptoms thereof, or stopping the symptoms of the disease or condition in a susceptible subject.

The term "subject" as used herein denotes animals, especially mammals. In one preferred embodiment, the term "subject" denotes "humans."

The term "therapeutically effective amount" as used herein refers to the amount of an active ingredient used alone or in combination with other treatments/medicaments for treating a disease or disorder. In the present disclosure, the term "therapeutically effective amount" refers to the amount of the antimicrobial agents that prevent the initiation of a bacterial infection, reduces symptoms of a bacterial infection, halts the progression of a bacterial infection, or causes another desired biological outcome (e.g., improvement in clinical symptoms, or the decrease/increase of lymphocyte and/or antibody levels). The effective amount of the antimicrobial peptides of the present invention may vary depending on factors such as the disease state, age, sex, and weight of the individual, and the ability of the antibody to elicit the desired response in the individual. A therapeutically effective amount is also the amount achieved where any toxic or detrimental effects of the antimicrobial peptides of the invention are outweighed by the therapeutically beneficial effects. The therapeutically effective amount of an active ingredient may be higher or lower, depending on the route of administration used. For example, when direct blood administration (e.g., sublingual, pulmonary, buccal, or intranasal delivery) is used, a lower dose of the active ingredient is administered.

In some embodiments, the therapeutically effective amount of the antimicrobial peptides of the present invention is about 0.1 to 500 mg/kg, preferably about 1 to 200 mg/kg, more preferably about 5 to 50 mg/kg, most preferably about 5 to 10 mg/kg. For the treatment of adults, dosages ranging from about 5 mg to 50 g per day can be used, depending on the route and frequency of administration. Effective doses for cell culture are generally between about 0.1 μM and about 1000 μM. In one embodiment, the effective dose for cell culture is between about 6.25 M and about 50 M.

As described herein, the terms "peptide properties", "peptide property," "physical properties of peptides," "physical characteristics for peptides" and "physicochemical properties" are used interchangeably. The use here of "peptide properties" indicates the physical characteristics for peptides, e.g., "net charge", "peptide length", "hydrophobic moment", "Boman Index", or "the ratio of secondary structure."

The antimicrobial peptides of the present invention can be incorporated into a pharmaceutical composition, which can be prepared by the methods generally known in the art, comprising a therapeutically effective amount of the antimicrobial peptides of the present disclosure and one or more pharmaceutically acceptable carriers, diluents, or excipients. The pharmaceutical compositions can be formulated for administration by oral or parenteral routes (e.g., subcutaneous, intravenous, intraperitoneal, intramuscular, or transdermal) for the therapeutic or prophylactic treatment of diseases, such as bacterial infections.

The pharmaceutical preparations disclosed herein can be prepared according to standard procedures and administered in doses that reduce, prevent, or eliminate infection (see, e.g., Remington's Pharmaceutical Sciences, Mack Publishing Company, Easton, PA; and Goodman and Gilman, "The Pharmaceutical Basis of Therapeutics," Pergamon Press, New York, NY, the contents of which are incorporated herein by reference for a general description of methods of administering various antimicrobial agents for human therapy).

Pharmaceutical compositions for oral administration can be in the form of, for example, lozenge, capsule, suspension, or liquid. For intravenous (IV) use, the pharmaceutical composition can be dissolved or suspended in any conventional intravenous fluid and administered by infusion. Suitable intravenous fluids include, but are not limited to, saline or Ringer's solution. Intravenous administration can be by, without limitation, syringe, micropump, or intravenous drip. Pharmaceutical compositions of the present invention for parenteral injection comprise pharmaceutically acceptable aqueous or non-aqueous solutions, dispersions, suspensions or emulsions, and sterile powders for reconstitution in sterile injectable solutions or dispersions prior to use. Examples of suitable aqueous and non-aqueous carriers, diluents, solvents or vehicles include water, ethanol, benzyl alcohol, polyols (e.g., glycerol, propylene glycol and polyethylene glycol), and suitable mixtures thereof, vegetable oils (e.g., corn oil or olive oil), and injectable organic esters (e.g., ethyl oleate). Proper fluidity can be maintained by the use of coating materials such as lecithin, by the maintenance of the desired particle size in dispersions, and by the use of surfactants. The compositions may also include various buffers.

The antimicrobial peptides of the invention can be used to treat individuals suffering from microbial infections, wherein the infection is caused or exacerbated by any type of bacteria or fungi, especially where caused by sensitive and multi-drug resistant bacteria.

In one embodiment, the bacterial infection may be caused or exacerbated by Gram-positive bacteria. Such Gram-positive bacteria include, but are not limited to, methicillin-susceptible *Staphylococcus* or methicillin-resistant *Staphylococcus* (e.g., *S. aureus*, *S. epidermidis*, *S. haemolyticus*, *S. hominis*, *S. saprophyticus* and coagulase-negative *Staphylococcus*), glycopeptide-intermediate *S. aureus* (GISA), vancomycin-resistant *S. aureus* (VRSA), penicillin-susceptible and penicillin-resistant Streptococci (e.g., *Streptococcus pneumoniae*, *S. pyogenes*, *S. agalactiae*, *S. avium*, *S. bovis*, *S. lactis*, *S. sangius*, Group C Streptococci, Group G Streptococci, and *Viridans* streptococci), *Enterococcus* (including vancomycin-sensitive and vancomycin-resistant strains, such as *Enterococcus faecalis* and *E. faecium*), *Clostridium difficile*, *C. clostridiiforme*, *C. innocuum*, *C. perfringens*, *C. ramosum*), *Listeria monocytogenes*, *Corynebacterium jeikeium*, *Bifidobacterium* spp., *Eubacterium* aerofaciens, *Eubacterium lentum*, *Lactobacillus acidophilus*, *L. casei*, *L. plantarum*, *Lactococcus* spp., *Leuconostoc* spp., *Pediococcus* spp., *Peptostreptococcus anaerobius*, P. asaccarolyticus, *P. magnus*, *P. micros*, *P. prevotii*, *P. productus*, *Propionibacterium acnes*, *Actinomyces* spp. and *Moraxella* spp.. (e.g., *M. catarrhalis*).

In one embodiment, the bacterial infection may be caused or exacerbated by Gram-negative bacteria. Examples of such Gram-negative bacteria include, but are not limited to, *Acinetobacter* spp. (e.g., *A. baumannii* and *A. haemolyticus*), *Actinobacillus actinomycetemcomitans*, *Achromobacter* spp. (e.g. *A. xylosoxidans* and *A. faecalis*), *Aeromonas* spp. (e.g. *A. hydrophila*), *Bacteroides* spp. (e.g., *B. fragilis*, *B. theataioatamicron*, *B. distasonis*, *B. ovatus* and B. vulgatus), *Bartonella* hensenae, *Bordetella* spp. (e.g., *B. pertussis*), *Borrelia* spp. (e.g., B. Burgdorferi), *Brucella* spp. (e.g., *B. melitensis*), *Burkholderia* spp. (e.g., *Burkholderia cepacia*, *Burkholderia pseudomallei* and B. mallei), *Campylobacter* spp. (e.g. *C. jejuni*, *C. fetus* and *C. coli*), Cedecea spp., *Chlamydia* spp. (e.g., *C. pneumoniae*, *C. trachomatis*), *Citrobacter* spp. (e.g., *C. diversus* and *C. freundii*), *Coxiella burnetii*, Edwardsiella spp. (e.g., E. tarda), *Ehrlichia chaffeensis*, *Eikenella corrodens*, *Enterobacter* spp. (e.g., *E. cloacae*, *E. aerogenes*, *E. agglomerans* and *E. coli*), *Francisella tularensis*, *Fusobacterium* spp., *Haemophilus* spp. (e.g. *H. influenzae* and *H. ducreyi*), *Helicobacter pylori*, *Kingella kingae*, *Klebsiella* spp. (e.g. *K. oxytoca*, *K. pneumoniae*, K. rhinoscleromatis and K. ozaenae), *Legionella pneumophila*, *Mannheimia haemolyticus*, *Moraxella catarrhalis*, *Morganella morganii*, *Neisseria* spp. (e.g., *N. gonorrhoeae* and *N. meningitidis*), *Pasteurella* spp. (such as *P. multocida*), *Plesiomonas shigelloides*, *Porphyromonas* spp. (e.g., *P. asaccharolytica*), *Prevotella* spp. (e.g., *P. corporis*, *P. intermedia* and P. endodontalis), *Proteus* spp. (e.g., *P. mirabilis*, *P. vulgaris*, *P. penneri* and *P. myxofaciens*), *Providencia* spp. (e.g. *P. stuartii*, *P. rettgeri* and *P. alcalifaciens*), *Pseudomonas* spp. (e.g., *P. aeruginosa*, carbapenem-resistant *Pseudomonas aeruginosa*, quinolone-resistant *Pseudomonas aeruginosa* and *P. fluorescens*); Ricketsia prowazekii, *Salmonella* spp. (e.g., *S. typhi* and S. paratyphi), *Serratia marcescens*, *Shigella* spp. (e.g., *S. flexneri*, *S. boydii*, *S. sonnei* and *S. dysenteriae*), *Streptobacillus moniliformis*, *Stenotrophomonas maltophilia*, *Treponema* spp., *Vibrio* spp. (e.g., *V. cholerae*, *V. parahaemolyticus*, *V. vulnificus*, *V. alginolyticus*) and *Yersinia* spp. (e.g., *Y. enterocolitica*, *Y. pestis* and *Y. pseudotuberculosis*).

Unless otherwise required by context, singular terms shall include the plural and plural terms shall include the singular.

EXAMPLES

In the present disclosure, several techniques are adopted to investigate the physical properties of each active antimicrobial peptide from the antimicrobial peptide database 3 (APD3, aps.unmc.edu/AP/main.php). First, bioinformatics tools are utilized to design α-helix and β-sheet antimicrobial peptides against both Gram-positive and gram-negative bacteria. A neural network-based bioinformatic prediction tool was used for the first stage evaluations of peptide properties. The antimicrobial peptides are de novo designed based on data mining using algorithm (i.e., decision trees for physical properties of peptides effective against different microorganisms ranging from Gram-positive and Gram-negative bacteria). Then, five peptides, e.g., three helical and two stranded, were bioinformatically designed and are synthesized by solid-phase synthesis. Whether the designed antimicrobial peptides have bactericidal efficacy is verified and the biosafety of the same is tested. Specifically, anti-bacterial abilities of the peptides were investigated with bactericidal assay and atomic force microscopy. In addition, hemolysis and mammalian cytotoxicity of the peptides were also measured to assess the safety of the peptides for use in animals. The present disclosure provided the validations of the efficacies of the antimicrobial peptides de novo designed based on the peptide properties mined from peptide database using algorithm. The experimental results indicated that the activity predications for effective peptides are currently fully efficacious for a-helical peptides. Accordingly, the methods disclosed herein demonstrate promising candidates and/or manners in design of peptide drugs, establishing the design rules of antimicrobial peptides, and verifying the effective design of antimicrobial peptides.

Example 1: Bioinformatic design of antimicrobial peptides

According to the decision tree rules previously developed in the inventor's laboratory (see FIG. 1), three novel peptides with a-helix structures (i.e., dK1, dK2, and dK3) and two novel peptides with B-stranded structures (i.e., dK4 and dK5) were designed, and HeliQuest (heliquest.ipmc.cnrs.fr/) was used to identify and calculate the peptide length, net charge and hydrophobic moment of α-helix structure peptides of the five peptides. The HNN secondary structure prediction tool (npsa-prabi.ibcp.fr/cgi-bin/npsa_automat.pl?page=/NPSA/npsa_hnn.html) was used for secondary structure prediction to understand the percentage of the specific secondary structure and the regional conformation of the peptides. The AMP Calculator and Predictor (aps.unmc.edu/prediction) available in APD3 was used to calculate the Boman index of the peptides. The results are shown in Tables 1 and 2.

TABLE 1

Sequences, secondary structure predictions and the peptide length of the antimicrobial peptides designed from decision tree results

| Peptides | Sequences and secondary structure predictions | Lengths |
|---|---|---|
| dK1 | IVRRIWRAWARRVRLVARIPAV (SEQ ID NO: 1) | 22 |
| (α-helix) | Chhhhhhhhhhhhhhhhhcccc | |
| dK2 | RLIAAWRAVIRARVRARRAPIF (SEQ ID NO: 2) | 22 |
| (α-helix) | Chhhhhhhhhhhhhhhhhcccc | |
| dK3 | RPFIVRAWRRAVARRARAILPI (SEQ ID NO: 3) | 22 |
| (α-helix) | Cchhhhhhhhhhhhhhhhhccc | |
| dK4 | FLPASFPAKFGPKLFCLVTKKC (SEQ ID NO: 4) | 22 |
| (β-sheet) | Cccccccccccceeeeeeccc | |
| dK5 | FLAIPSKPLKVAKPLGFALIIL (SEQ ID NO: 5) | 22 |
| (β-sheet) | Cccccccccccccceeeeeec | |

In the table, "h" represents predicted helical structures, "c" represents random structures, "e" represents predicted extended strand structures, and "lengths" represents the lengths of the peptides.

TABLE 2

Physicochemical properties and secondary structure predictions of the antimicrobial peptides designed according to decision tree rules

| Peptides | mH | Charge | Boman index (Kcal/mol) | Secondary structure predictions (%) | | |
|---|---|---|---|---|---|---|
| | | | | Helix | Extended | Coil |
| dK1 | 0.556 | +7 | 2.57 | 77.27 | 0 | 22.73 |
| dK2 | 0.309 | +7 | 2.75 | 77.27 | 0 | 22.73 |
| dK3 | 0.308 | +7 | 2.83 | 77.27 | 0 | 22.73 |
| dK4 | 0.161 | +4 | −0.43 | 0 | 27.27 | 72.23 |
| dK5 | 0.262 | +3 | −1.62 | 0 | 27.27 | 72.23 |

I

In Table 2, "mH" represents the hydrophobic moment of the peptide, "Charge" is the sum of the charges of the peptide in an electrically neutral environment, "Boman index" is the Bowman index, which is the estimated value of the binding potential of the peptide to other proteins, and "Secondary structure predictions (%)" is the secondary structure prediction.

The three α-helix structure peptides are all 22 amino acids in length, and all have +7 charges, and the predicted percentages of α-helix structure are all 77.27%. The Bowman indices of dK1, dK2 and dK3 are respectively 2.57 kcal/mol, 2.75 kcal/mol and 2.83 kcal/mol, and the hydrophobic moments thereof are 0.556, 0.309, and 0.308, respectively. The peptides of the other two β-stranded structures are both 22 amino acids in length, the predicted percentages of the β-stranded structures are both 27.27%, and the charges of dK4 and dK5 are +4 and +3, respectively. The five designed antimicrobial peptides as noted all conform to the rules of the decision tree.

Example 2: Synthesis and purification of antimicrobial peptides

The five antimicrobial peptides (dK1 to dK5) designed as noted were synthesized using a standard 9-fluorenyl methoxy carbonyl (F-moc) solid-phase synthesis technique on an automatic peptide synthesizer (433A, Applied Biosystems, MA, USA). The synthesized peptides were purified using a reverse-phase high-performance liquid chromatography (HPLC) instrument (Waters 600, MA, USA) equipped with a preparative reverse-phase column (XBridge BEH 130 Prep C18 Column, 10 μm OBD 19×250 mm, Waters, MA, USA). The purities of purified peptides (i.e., dK1, dK2, dK3, dK4 and dK5) were over 95%.

Example 3: Bactericidal Assay

The antimicrobial activities of dK1, dK2, dK3, dK4 and dK5 were determined by bactericidal assays on laboratory strains of MRSA (methicillin-resistant *Staphylococcus aureus*) and MDRAB (multidrug-resistant *Acinetobacter baumannii*).

The bacteria were inoculated in Luria broth (LB) solid medium (BioShop Canada Inc., Ontario, Canada) (Focus Bioscience, Murrarrie, Australia). Single colonies were collected and inoculated in 8 mL of liquid medium, and the cultures were incubated overnight at 37° C., 200 rpm. On the next day, the bacterial cultures were centrifuged with a centrifuger (KUBOTA2800, KUBOTA, Osakashi, Japan) at 2500 rpm for 5 minutes at room temperature, and the supernatants were discarded. The pellets were mixed and suspended with 1×PBS (phosphate-buffered saline, PBS, pH 7.4) (PROTECH, Taipei, Taiwan). The step was repeated twice to wash the bacterial cells. After the washing step, the bacterial cells were then re-suspended in 1×PBS, and the concentrations of bacterial cells were adjusted to $1 \times 10^7$ CFU/mL.

In the bactericidal assay, 2700 μL of 1× PBS were mixed with 300 μL $1 \times 10^7$ CFU/mL bacteria suspension mentioned as negative control, and each of the solutions of dK1 to dK5 at different concentrations was mixed with 300 μL $1 \times 10^7$ CFU/mL bacteria suspension and 2700 μL of 1× PBS. The mixtures were incubated at 37° C., 200 rpm for 2 hours. After incubation, 100 μL of each of the control group samples and the experimental group samples were collected and put in Eppendorf centrifuge tubes, and followed by 10-fold serial dilution with 900 μL of 1× PBS. After the serial dilution, 100 μL of the sample from each group was inoculated on the LB solid medium. The experiments were carried out in triplicate for each group, and the LB solid media with samples were cultured at 37° C. for at least 18 hours. After overnight incubation at 37° C., bacterial colonies were counted. Bacterial survival rates of each group were determined as follows.

% survival rate=[(Colonies formed from peptide-treated sample)/(Colonies formed from negative control)]×100%

Figure 2:
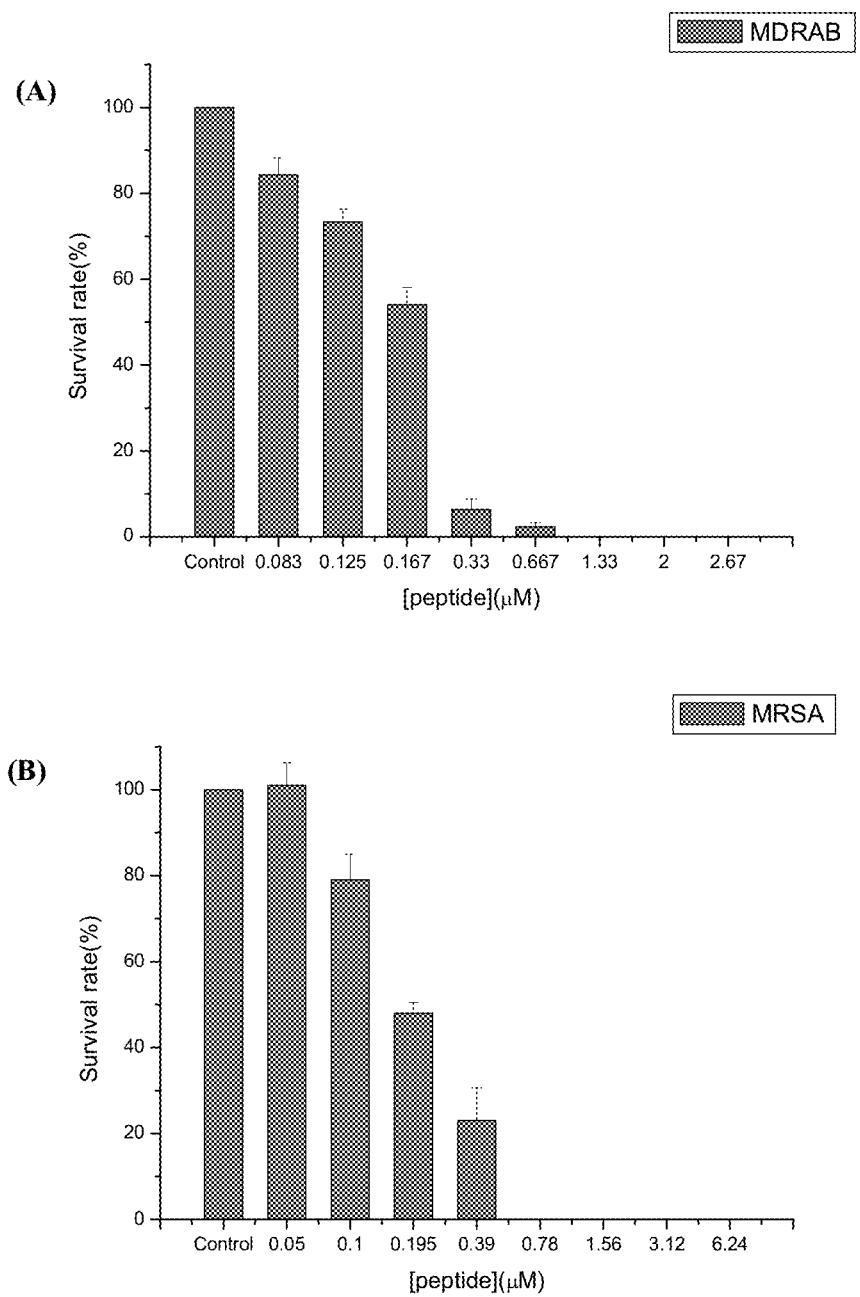
FIG. 2 shows the dK1 bactericidal assay results. (A) Bactericidal assay results of dK1 against Gram-negative bacteria MDRAB; (B) Bactericidal assay results of dK1 against Gram-positive bacteria MRSA. The bactericidal results of antimicrobial peptide dK1 showed that the $IC_{50}$ of MRSA was about 0.195 μM, the MBC was between 0.39 to 0.78 μM, the $IC_{50}$ of MDRAB was about 0.167 μM, and the MBC of MDRAB was between 0.667 to 1.33 μM.
Figure 3:
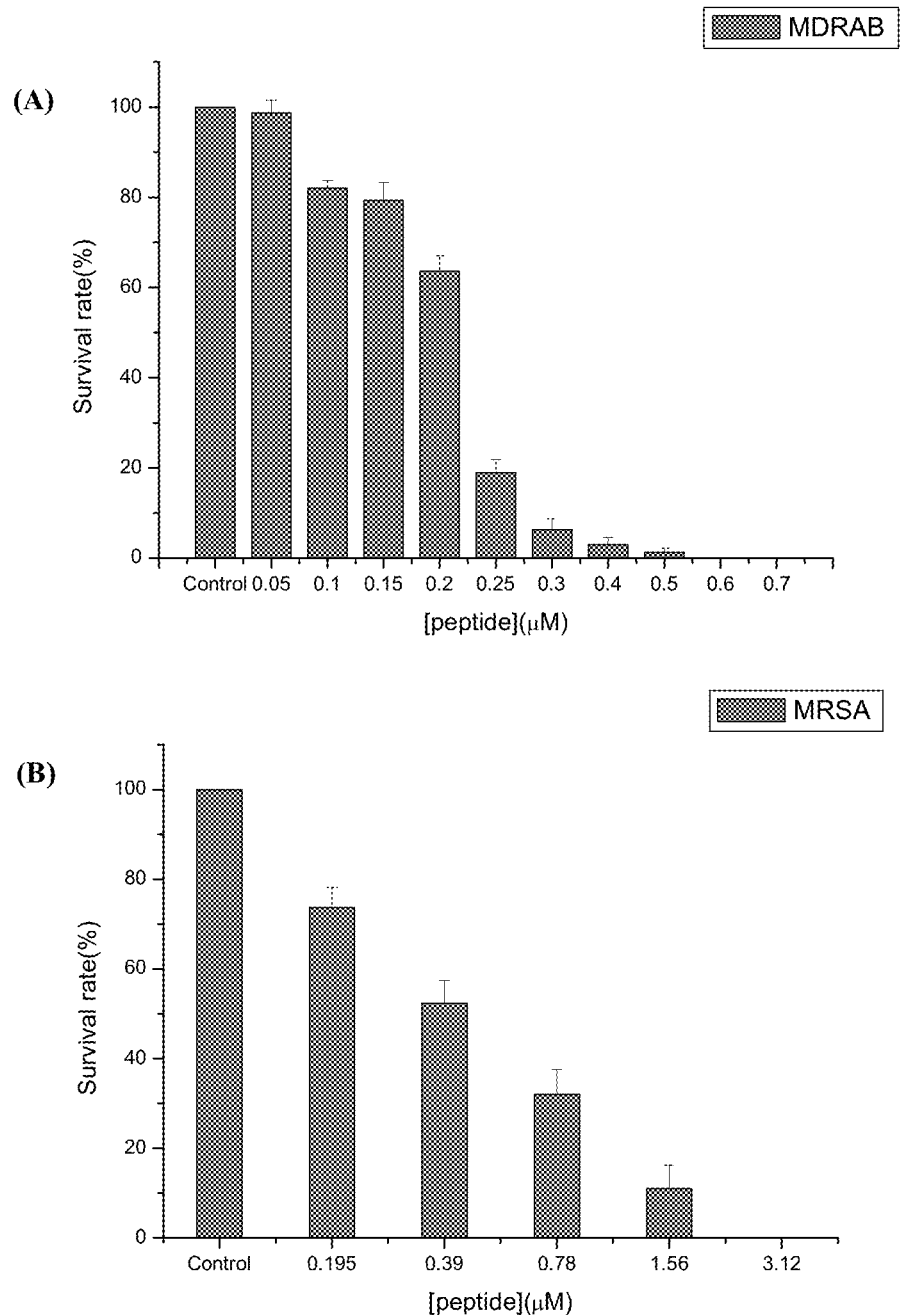
FIG. 3 shows the dK2 bactericidal assay results. (A) Bactericidal assay results of dK2 against Gram-negative bacteria MDRAB; (B) Bactericidal assay results of dK2 against Gram-positive bacteria MRSA. The bactericidal results of antimicrobial peptide dK2 showed that the $IC_{50}$ of MRSA was about 0.39 μM, the MBC was between 1.56 to 3.12 µM, the $IC_{50}$ of MDRAB was about 0.2 to 0.25 µM, and the MBC of MDRAB was between 0.5 to 0.6 µM.
Figure 4:
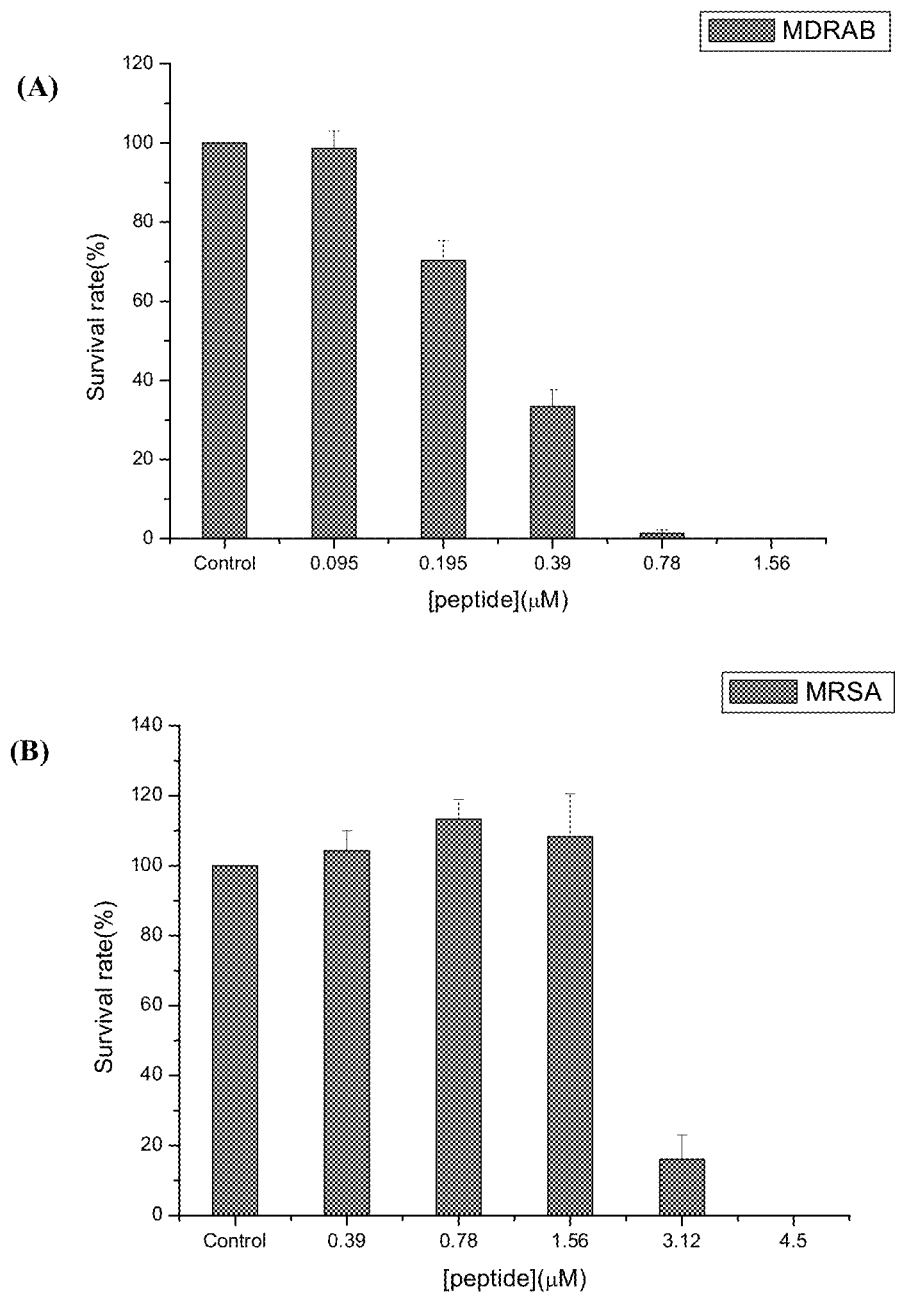
FIG. 4 shows the dK3 bactericidal assay results. (A) Bactericidal assay results of dK3 against Gram-negative bacteria MDRAB; (B) Bactericidal assay results of dK3 against Gram-positive bacteria MRSA. The bactericidal results of antimicrobial peptide dK3 showed that the $IC_{50}$ of MRSA was about 1.56 to 3.12 µM, the MBC was between 3.12 µM to 4.5 µM, the $IC_{50}$ of MDRAB was about 0.195 to 0.39 µM, and the MBC of MDRAB was between 0.78 to 1.56 µM.

The designed peptides dK1, dK2 and dK3 (α-helix structure) were initially tested for their bactericidal activities against the Gram-positive bacteria MRSA and Gram-negative bacteria MDRAB, and the results are shown in FIGS. 2 to 4. As shown in FIG. 2, the $IC_{50}$ of dK1 against Gram-positive bacteria MRSA was about 0.195 µM, and the minimum bactericidal concentration (MBC) was 0.39 to 0.78 µM; the $IC_{50}$ of dK1 against MDRAB was approximately 0.167 µM, and the MBC was 0.667 to 1.33 µM. As shown in FIG. 3, the $IC_{50}$ of dK2 against MRSA was about 0.39 µM, and the MBC was 1.56 to 3.12 µM; the $IC_{50}$ of dK2 against MDRAB was about 0.2 to 0.25 µM, and the MBC was 0.5 to 0.6 µM. As shown in FIG. 4, the $IC_{50}$ of dK3 against MRSA was 1.56 to 3.12 µM, and the MBC was 3.12 to 4.5 µM. The bactericidal activity of dK3 against MRSA was weaker than that of dK1 and dK2, while the $IC_{50}$ thereof against MDRAB was about 0.195 to 0.39 µM, and the MBC was 0.78 to 1.56 µM. To sum up, the antimicrobial peptides with α-helix structure against Gram-positive bacteria and Gram-negative bacteria designed according to the decision tree rules performed quite well in the bactericidal assay.

Figure 5:
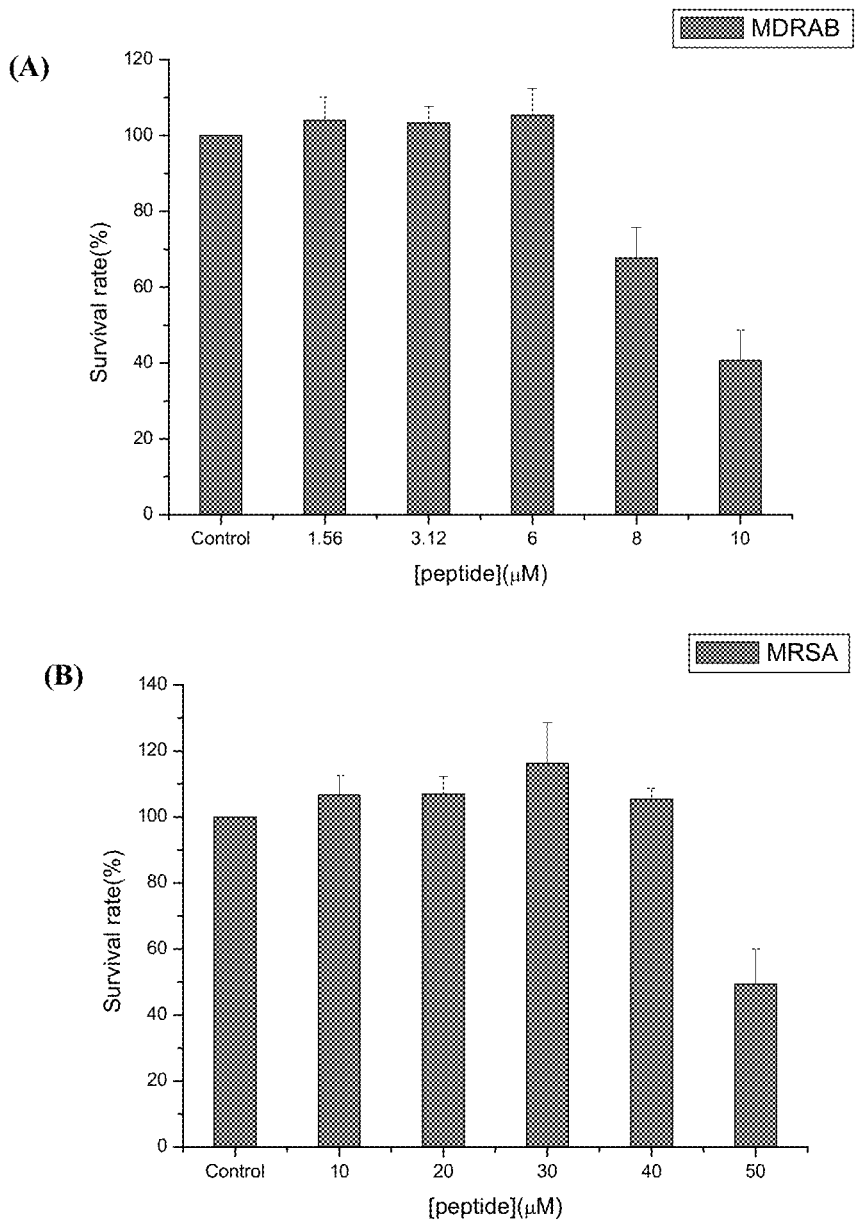
FIG. 5 shows the dK4 bactericidal assay results. (A) Bactericidal assay results of dK4 against Gram-negative bacteria MDRAB; (B) Bactericidal assay results of dK4 against Gram-positive bacteria MRSA. The bactericidal results of antimicrobial peptide dK4 showed that the $IC_{50}$ of MRSA was larger than 50 µM, the MBC was larger than 50 µM, the $IC_{50}$ of MDRAB was about 8~10 µM, and the MBC of MDRAB was larger than 10 µM.
Figure 6:
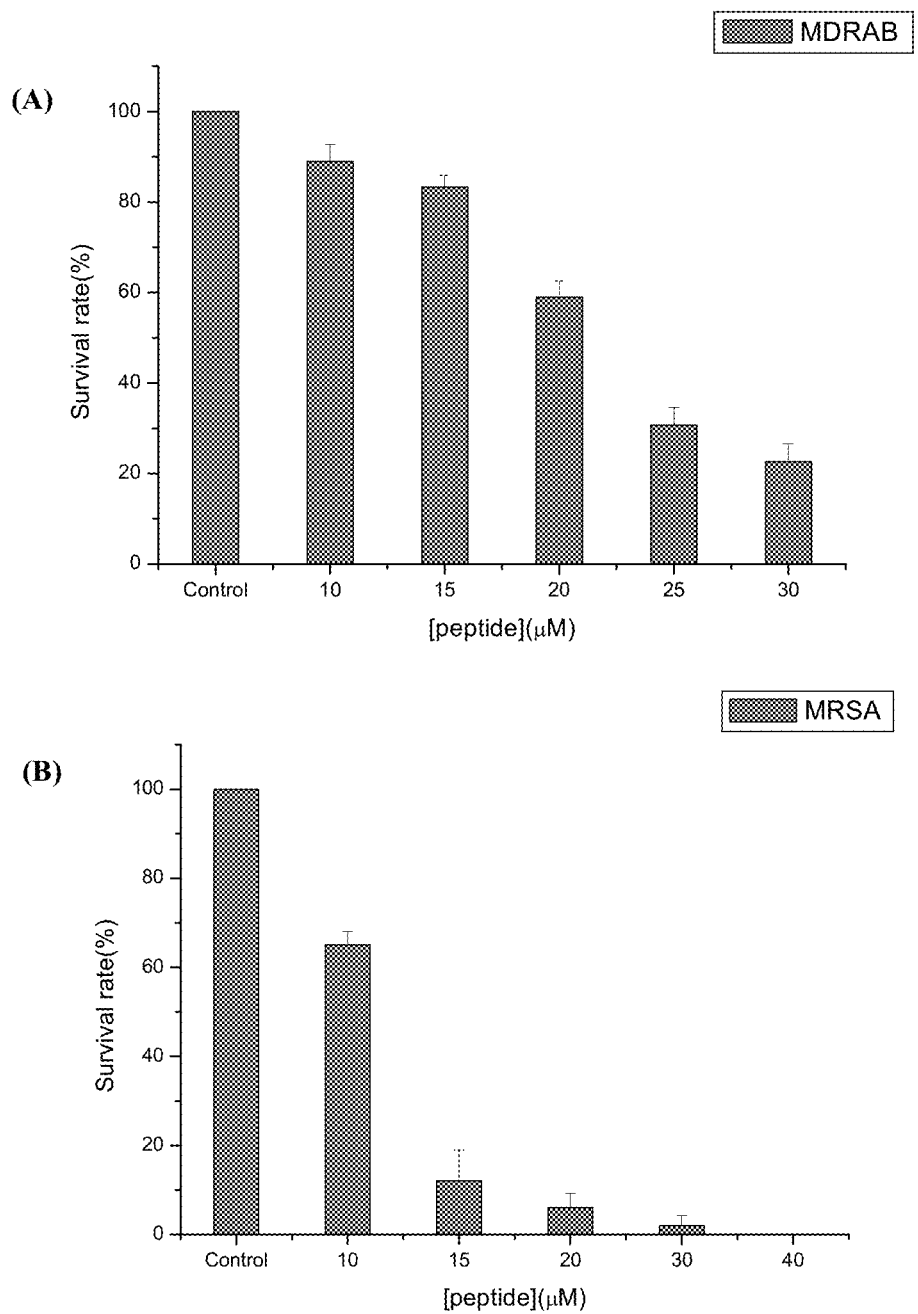
FIG. 6 shows the dK5 bactericidal assay results. (A) Bactericidal assay results of dK5 against Gram-negative bacteria MDRAB; (B) Bactericidal assay results of dK5 against Gram-positive bacteria MRSA. The bactericidal results of antimicrobial peptide dK5 showed that the $IC_{50}$ of MRSA was about 10 to 15 µM, the MBC was about 30 to 40 µM, the $IC_{50}$ of MDRAB was about 20 to 25 µM, and the MBC of MDRAB was larger than 30 µM.
Figure 7:
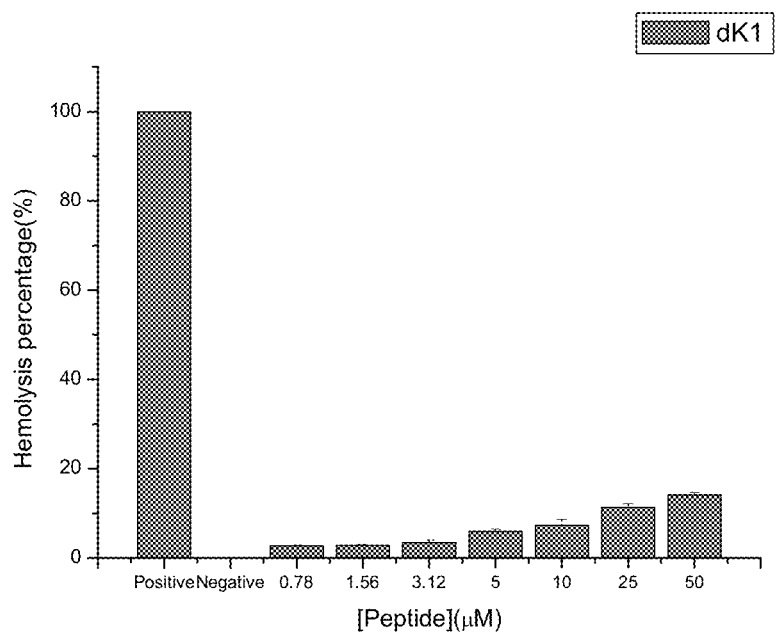
FIG. 7 shows the dK1 hemolysis assay results on mammalian erythrocytes. In this hemolysis assay, the positive control group was regarded as 100% and the negative control group was regarded as 0% to calculate the hemolysis percentage. The results showed that the anti-microbial peptide dK1 did not have strong hemolysis activity on mammalian erythrocytes.
Figure 8:
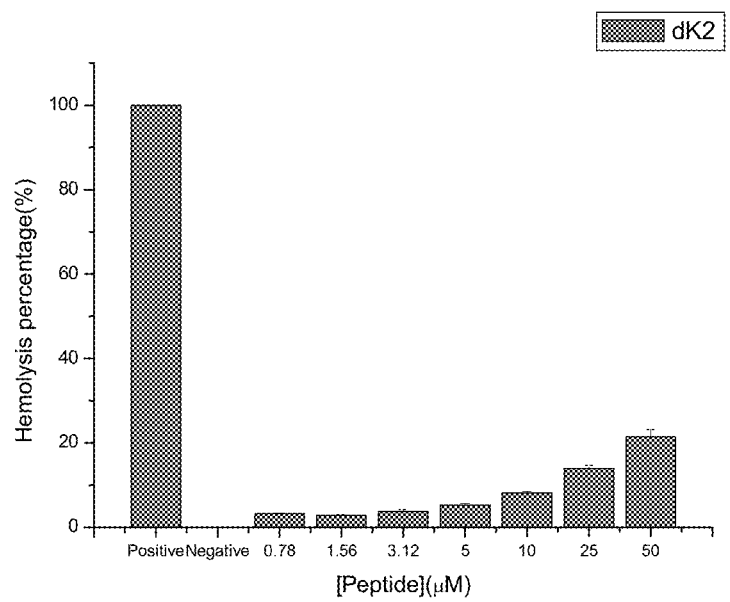
FIG. 8 shows the dK2 hemolysis assay results on mammalian erythrocytes. In this hemolysis assay, the positive control group was regarded as 100% and the negative control group was regarded as 0% to calculate the hemolysis percentage. The results showed that the anti-microbial peptide dK2 did not have strong hemolysis activity on mammalian erythrocytes.
Figure 9:
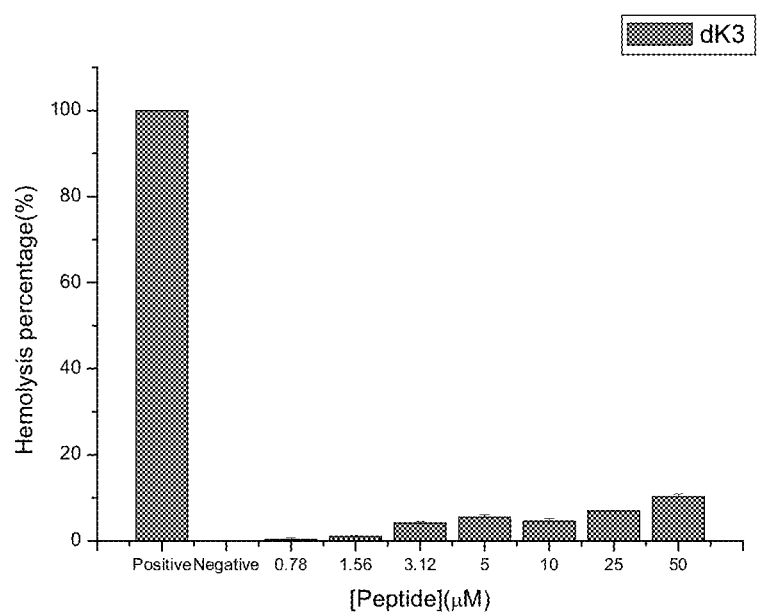
FIG. 9 shows the dK3 hemolysis assay results on mammalian erythrocytes. In this hemolysis assay, the positive control group was regarded as 100% and the negative control group was regarded as 0% to calculate the hemolysis percentage. The results showed that the anti-microbial peptide dK3 did not have strong hemolysis activity on mammalian erythrocytes.
Figure 10:
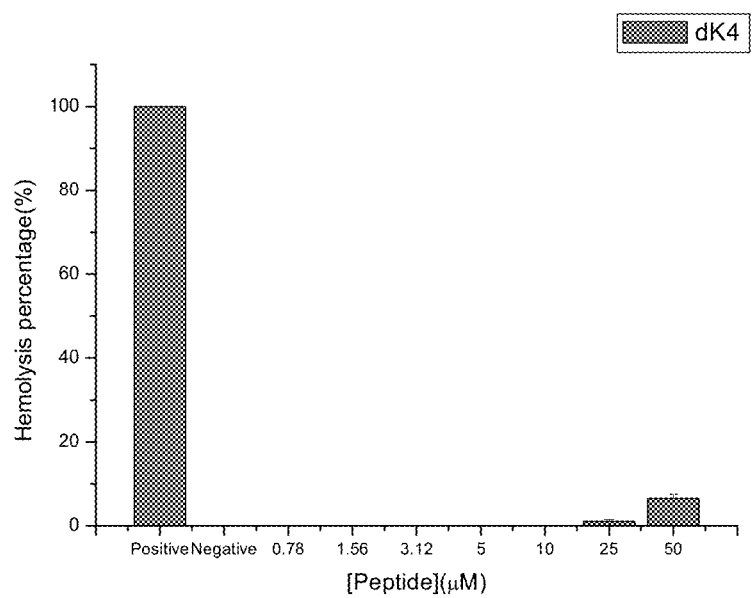
FIG. 10 shows the dK4 hemolysis assay results on mammalian erythrocytes. In this hemolysis assay, the positive control group was regarded as 100% and the negative control group was regarded as 0% to calculate the hemolysis percentage. The results showed that the anti-microbial peptide dK4 did not have strong hemolysis activity on mammalian erythrocytes.
Figure 11:
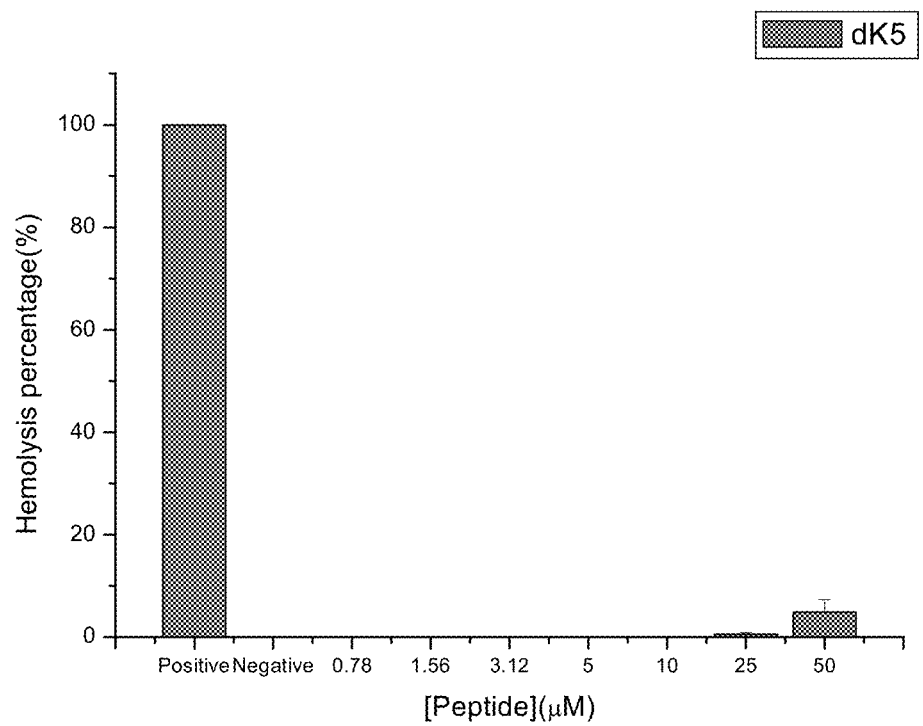
FIG. 11 shows the dK5 hemolysis assay results on mammalian erythrocytes. In this hemolysis assay, the positive control group was regarded as 100% and the negative control group was regarded as 0% to calculate the hemolysis percentage. The results showed that the anti-microbial peptide dK5 did not have strong hemolysis activity on mammalian erythrocytes.

Likewise, the designed peptides dK4 and dK5 with β-stranded structure were tested for their bactericidal activities against the Gram-positive bacteria MRSA and Gram-negative bacteria MDRAB, and the results thereof are shown in FIGS. 5 and 6. As shown in FIG. 5, the $IC_{50}$ of dK4 against MRSA was about 50 µM, and the MBC was greater than 50 µM; the $IC_{50}$ of dK4 against MDRAB was about 8~10 µM, and the MBC was greater than 10 µM. As shown in FIG. 6, the $IC_{50}$ of dK5 against MRSA was about 10 to 15 µM, and the MBC was about 30 to 40 µM; the $IC_{50}$ of dK5 against MDRAB was about 20 to 25 µM, and the MBC was higher than 30 µM. The experimental results in this case show that the bactericidal activities of dK4 and dK5 having β-stranded structures are weaker than those of dK1, dK2 and dK3 having α-helix structures.

The weak bactericidal activities of dK4 and dK5 may result from disproportionate numbers of samples with different secondary structures (e.g., α-helix structure or β-stranded structure) in the database or simply the disparity among various secondary structures. In the APD3 antimicrobial peptide database, the number of samples of β-stranded antimicrobial peptides and that of α-helix antimicrobial peptides is significantly different [see Wang, G., Li, X. & Wang, Z., 2016], and a small number of samples would cause problems in data mining, which may be one of the reasons for the less precise decision tree rules for β-stranded antimicrobial peptides.

Example 4: Peptide hemolysis assays

The evaluation of biosafety is crucial for new drug marketing [see Oddo, A. and P.R. Hansen, "Hemolytic Activity of Antimicrobial Peptides." *Methods Mol Biol,* 2017. 1548: p. 427-435.]. Toxicity can be classified into three types, namely, hemolytic toxicity, cytotoxicity and immunotoxicity [see Timmons, P. B. and C. M. Hewage, "HAPPENN is a novel tool for hemolytic activity prediction for therapeutic peptides which employs neural networks." *Sci Rep,* 2020. 10(1): p. 10869.]. In the present disclosure, hemolytic toxicity and cytotoxicity were assessed. In the hemolysis assays, the heme concentrations in the samples were measured after red blood cells interacted with the antimicrobial peptides.

Positive control and negative control were used in the hemolysis assays. The positive control is a mixture of 2% red blood cells, 1% Triton X-100 (MP Biomedicals, South Carolina, United State) and 97% 1×PBS solution, and the negative control is a mixture of 2% red blood cells and 98% 1×PBS solution. The final volume of the sample solutions in the above control groups were 200 µL. The test groups contain 100 µL of the antimicrobial peptide solutions at different concentrations, 2% red blood cell concentrate and 98% 1×PBS. The control group samples and test group samples in Eppendorf centrifuge tubes were incubated at 37° C. for 2 hours, and then centrifuged at 1000 g, 4° C., 5 minutes. 100 µL of the supernatant from the samples were collected and put in a 96-well assay microplate, and the ELISA Reader (EPOCH™, BioTek instruments, Inc., Winooski, United State) was used to detect the hemoglobin in the supernatant was measured at the wavelength of 415 nm. The higher the $OD_{415}$ value, the higher degree of hemolysis.

The blood samples treated with 1% Triton X-100 were used as positive controls and were determined to have 100% hemolysis. The percentages of hemolysis induced by the test peptides were calculated as follows.

$$[(A_p - A_c)/(A_T - A_c)] \times 100\%$$

where $A_p$ is the absorbance of a peptide-treated sample; $A_c$ is the absorbance of an untreated control (negative control) sample; and $A_T$ is the absorbance of a Triton X-100 –treated sample (positive control).

In the hemolysis assay, the antimicrobial peptides from low concentration to high concentration are prepared (i.e., 0.78 µM, 1.56 µM, 3.12 µM, 5 µM, 10 µM, 25 µM and 50 µM) so that the hemolysis activities of each peptide at different concentrations are separately tested. The results are shown in FIGS. 7-11.

According to the results of the test groups with the lowest concentration (0.78 µM), dK2 had the highest hemolysis percentage of about 3%. In the test groups with the highest concentration (50 µM), dK2 also had the highest hemolysis percentage of about 21%. In view of the bactericidal assay results obtained from Example 3, dK1, dK2 and dK3 have very weak hemolytic activity under the effective bactericidal concentration.

Although the hemolytic activities of dK4 and dK5 were also quite weak, in view of the bactericidal assay results, dK4 and dK5 require higher concentrations to achieve bactericidal potency comparable to that of dK1, dK2 and dK3. In this connection, dK4 and dK5 may not be the preferable drug candidates.

Example 5: Cytotoxicity Assay on Mammalian Cells

For measuring the cytotoxicity of the antimicrobial peptides dK1, dK2 and dK3, a colorimetric 3-bis-(2-methoxy-4-nitro-5-sulfophenyl)-2H-tetrazolium-5-carboxanilide (XTT) dye reduction assay was employed. The cytotoxicity of the antimicrobial peptides of the invention were tested on Huh-7 and HeLa cells. The culture medium for Huh-7 is Dulbecco's modified eagle medium, DMEM (Gibco™, NY, USA) containing 10% fetal bovine serum (FBS) (Gibco™, NY, USA) 1% non-essential amino acid solution (NEAA) (Biological Industries, Beit HaEmek, Israel) and 1% streptomycin-penicillin solution (Gibco™, NY, USA). The culture medium for HeLa cells is Minimum Essential Medium (MEM) (Gibco™, NY, USA) containing 10% FBS (Gibco™, NY, USA), 1% sodium pyruvate (Gibco™, NY, USA), 1% NEAA (Biological Industries, Beit HaEmek, Israel) and 1% streptomycin-penicillin (Gibco™, NY, USA).

In the XTT cytotoxicity test, Triton X-100 was used as the positive control, and the negative control group only contains the cells and XTT reagent (Biological Industries, Beit HaEmek, Israel). On the first day, 100 µL of cells at a concentration of $1 \times 10^5$ cells/mL were added to each well of a 96-well assay microtiter plate, and then placed in a 37° C., 5% CO2 incubator overnight to let the cells adhere to the wall of the well plate. On the next day, the medium was removed from all wells. In the positive control group, 1 μL Triton X-100, 99 μL cell culture medium and 100 μL XTT reagent were added to each well. In the negative control group, 100 μL cell culture medium and 100 μL XTT reagent were added to each well. In the experimental group, 100 μL, 4 μM antimicrobial peptide solution and 100 μL XTT reagent were added to each well, wherein the antimicrobial peptide solutions were prepared by dissolving antimicrobial peptide powders in the cell culture medium.

The cells were cultured in cell culture medium containing each antimicrobial peptide at 2 μM peptide concentration and XTT reagent. The absorbance of the samples was measured at the $4^{th}$ hour, and cell viability calculated to evaluate the cytotoxicity of the antimicrobial peptides. The absorbance of the samples was measured with an ELISA reader (EPOCH™, BioTek instruments, Inc., Winooski, USA) at a wavelength of 475 nm.

The absorbance value of the positive control group was regarded as 0% cell viability, and the absorbance value of the negative control group was regarded as 100% cell viability. In the cytotoxicity assay, the calculation method is similar to that of the hemolysis assay method, which is as follows.

$$\text{cell viability} = [(OD_{475} \text{of experimental group} - OD_{475} \text{negative control group})/(OD_{475} \text{of positive control group} - OD_{475} \text{of negative control group})] \times 100\%$$

Figure 12:
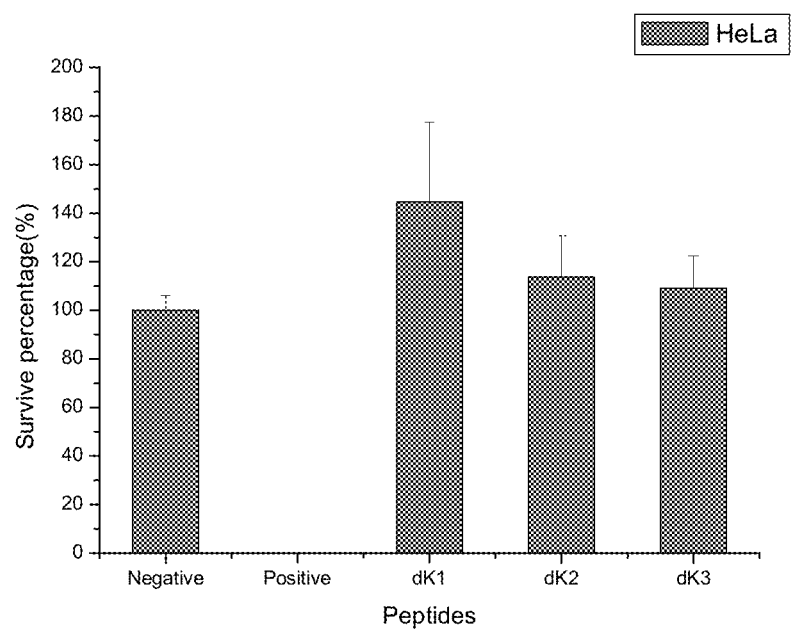
FIG. 12 shows the cytotoxicity assay results of dK1, dK2 and dK3 on Hela cells. In this cytotoxicity assay, the negative control group was regarded as 100% and the positive control group was regarded as 0% to calculate the cell viability. The experimental results showed that the antimicrobial peptides dK1, dK2 and dK3 were not very toxic to HeLa.
Figure 13:
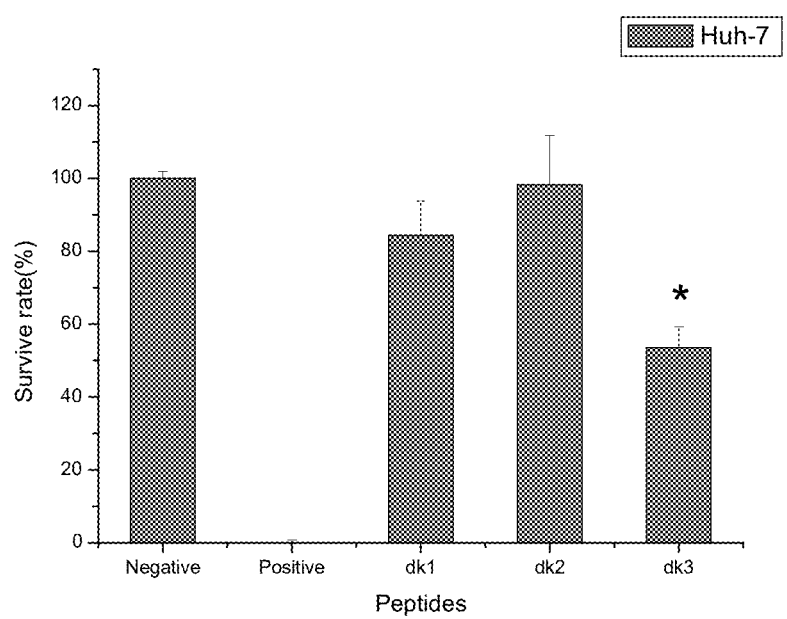
FIG. 13 shows the cytotoxicity assay results of dK1, dK2 and dK3 on Huh-7 cells. In this cytotoxicity assay, the negative control group was regarded as 100% and the positive control group was regarded as 0% to calculate the cell viability. The experimental results showed that the antimicrobial peptides dK1 and dK2 were not very toxic to Huh-7. While dK3 showed a 50% reduction in cell viability against Huh-7 cells, it is demonstrated that dK3 may have an anticancer potential in cytotoxicity experiments. *represents a significant difference between this group and the control group, p<0.05.

The results are shown in FIGS. 12 and 13. For HeLa cells, the three antimicrobial peptides (dK1, dK2 and dK3) have very low, or even zero, toxicity, at the effective antibacterial concentration. It showed that dK1, dK2 and dK3 have almost no cytotoxicity to HeLa cells under the effective antibacterial concentrations against MDRAB and MRSA; however, in terms of Huh-7 cells, dK1 and dK2 are less toxic. Unexpectedly, dK3 was more cytotoxic to Huh-7 cells. After Huh-7 cells exposed to 2 μM dK3 in cell culture medium for four hours, only about half of Huh-7 cells survived.

In this part of the experiment, these three peptides were almost non-cytotoxic to HeLa cells, while in terms of Huh-7, dK1 and dK2 do not have significant cytotoxicity, and it was surprisingly found that dK3 may have potential for anti-HCC (hepatocellular carcinoma) activity.

Accordingly, among the five peptides designed based on the physical properties obtained from the algorithm methods, all the designed α-helical peptides exhibited fully efficacious activity. However, the two β-stranded peptides were less effective. That is, the three α-helical peptides have broad-spectrum bactericidal activity against both Gram-positive and Gram-negative bacteria and low hemolytic and cytotoxic activity on mammalian cells.

Numerous modifications and variations of the invention as set forth in the illustrative examples are expected to occur to those skilled in the art. Consequently, only such limitations as appear in the appended claims should be placed on the invention.

What is claimed is:

1. An antimicrobial peptide comprising the an amino acid sequence of SEQ ID NO: 1.

2. A composition comprising the antimicrobial peptide of claim 1.

3. An antimicrobial agent comprising the composition of claim 2.

4. The antimicrobial agent of claim 3, wherein the antimicrobial agent is a medicine or an additive for food or feed.

5. A nucleic acid molecule encoding the antimicrobial peptide of claim 1.

6. A host cell comprising the nucleic acid molecule of claim 5.

7. A method of preparing the antimicrobial peptide of claim 1 comprising synthesizing the antimicrobial peptide by solid-phase synthesis, and purifying the antimicrobial peptide.

8. A method of treating a bacterial infection comprising administering a therapeutically effective amount of the composition of claim 2 to a subject in need thereof.

9. The method of claim 8, wherein the bacterial infection is a Gram-positive or Gram-negative bacterial infection.

\* \* \* \* \*